(12) United States Patent
Willey et al.

(10) Patent No.: US 9,834,740 B2
(45) Date of Patent: Dec. 5, 2017

(54) PHOTOACTIVATORS

(71) Applicant: The Procter & Gamble Company, Cincinnati, OH (US)

(72) Inventors: Alan David Willey, Cincinnati, OH (US); Jacob Robert Adams, Cincinnati, OH (US); Kady Lynn Willison, Cincinnati, OH (US); Kenneth Edward Yelm, Hamilton, OH (US); Gregory Mark Bunke, Lawrenceburg, IN (US); Robb Richard Gardner, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/594,190

(22) Filed: Jan. 12, 2015

(65) Prior Publication Data

US 2015/0210960 A1   Jul. 30, 2015

Related U.S. Application Data

(60) Provisional application No. 61/930,999, filed on Jan. 24, 2014.

(51) Int. Cl.
| | |
|---|---|
| *C11D 3/48* | (2006.01) |
| *C11D 3/42* | (2006.01) |
| *C11D 3/00* | (2006.01) |
| *C07D 335/16* | (2006.01) |
| *C11D 3/34* | (2006.01) |

(52) U.S. Cl.
CPC .......... *C11D 3/0063* (2013.01); *C07D 335/16* (2013.01); *C11D 3/3481* (2013.01); *C11D 3/42* (2013.01); *C11D 3/48* (2013.01)

(58) Field of Classification Search
CPC .................. C11D 3/0063; C11D 3/48
See application file for complete search history.

(56) References Cited

U.S. PATENT DOCUMENTS

| | | |
|---|---|---|
| 3,393,153 A | 7/1968 | Zimmerer et al. |
| 3,635,828 A | 1/1972 | Benjamin et al. |
| 3,714,151 A | 1/1973 | Lyness |
| 3,916,652 A | 11/1975 | Speakman |
| 3,927,967 A | 12/1975 | Speakman |
| 4,332,691 A | 6/1982 | Beavan |
| 4,524,014 A | 6/1985 | Finch et al. |
| 4,526,700 A | 7/1985 | Hensley |
| 4,602,097 A * | 7/1986 | Curtis .................. C07D 335/16 522/117 |
| 4,985,559 A | 1/1991 | Goldberg et al. |
| 4,990,280 A | 2/1991 | Thorengaard et al. |
| 5,057,236 A | 10/1991 | Petrin et al. |
| 5,082,578 A | 1/1992 | Langer et al. |
| 5,236,464 A | 8/1993 | Green et al. |
| 5,330,672 A | 7/1994 | Langer et al. |
| 5,332,014 A | 7/1994 | Feig |
| 5,697,230 A | 12/1997 | Ender et al. |
| 5,834,412 A | 11/1998 | Rohrbaugh et al. |
| 6,150,494 A | 11/2000 | Wang et al. |
| 6,524,529 B1 | 2/2003 | Horton |
| 7,081,225 B1 | 7/2006 | Hollander |
| 2004/0171505 A1 | 9/2004 | Nonami |
| 2004/0259023 A1 | 12/2004 | Campagnola et al. |
| 2004/0259747 A1 | 12/2004 | Schmidt et al. |
| 2004/0266648 A1 | 12/2004 | Willey et al. |
| 2005/0126609 A1 | 6/2005 | Son et al. |
| 2005/0150528 A1 | 7/2005 | Kim |
| 2005/0155633 A1 | 7/2005 | Daume et al. |
| 2006/0097222 A1 | 5/2006 | Doona et al. |
| 2007/0214577 A1 | 9/2007 | Bianchetti et al. |
| 2009/0090387 A1 | 4/2009 | Massey-Brooker |
| 2009/0145452 A1 | 6/2009 | Anderson et al. |
| 2009/0170744 A1 | 7/2009 | Meine et al. |
| 2009/0194474 A1 | 8/2009 | Tranchant et al. |
| 2011/0057123 A1 | 3/2011 | Ho |
| 2011/0180118 A1 | 7/2011 | Schrott |
| 2011/0215689 A1 | 9/2011 | Wegener |
| 2011/0217202 A1 | 9/2011 | Winterton |
| 2011/0315709 A1 | 12/2011 | Fileccia et al. |
| 2012/0055513 A1 | 3/2012 | Eglmeier et al. |
| 2012/0093905 A1 | 4/2012 | Batchelor et al. |
| 2013/0032610 A1 | 2/2013 | Muller |

(Continued)

FOREIGN PATENT DOCUMENTS

| | | |
|---|---|---|
| CA | 2079358 A1 | 3/1993 |
| DE | 2335570 A1 | 1/1974 |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Okubayashi et al, Journal of Applied Polymer Science, Improvement of Wettability of Hydrophobic Films by Impregnation of Anthraquinone Attached to Polyoxyethylene Glycol, 2005, vol. 97, pp. 545-549.*
Allen et al, European. Polymer Journal, Photochemistry of Thioxanthones-III Spectroscopic and Flash Photolysis Study on Hydroxy and Methoxy Derivatives, 1986, vol. 22, No. 9, pp. 691-697.*
Corrales et al, Journal of Photochemistry and Photobiology A: Chemistry, Novel water soluble copolymers based on thioxanthone: photochemistry and photoinitiation activity 2005,169, pp. 95-100.*
Corrales et al, Journal of Photochemistry and Photobiology A: Chemistry, Free radical macrophotoinitiators: an overview on recent advances, 2003,159, pp. 103-114.*

(Continued)

*Primary Examiner* — Paul A Zucker
(74) *Attorney, Agent, or Firm* — Jason J Camp

(57) ABSTRACT

Photoactivators comprise a photoactive moiety and a hydrophilic moiety. The photoactivators preferably comprise less than about 35%, by weight of the photoactivator, of the photoactive moiety. The photoactivators can be activated to a photo-excited state by excitation with incident radiation of a wavelength between about 350 nm and 750 nm, preferably between about 350 nm and about 420 nm. The photoactivators further encompass those having certain chemical formulations.

8 Claims, 1 Drawing Sheet

(56) References Cited

U.S. PATENT DOCUMENTS

| | | |
|---|---|---|
| 2013/0288942 A1 | 10/2013 | Stenger |
| 2014/0084024 A1 | 3/2014 | Benda |
| 2014/0142302 A1 | 5/2014 | Furuyama et al. |
| 2014/0166829 A1 | 6/2014 | Thompson |

FOREIGN PATENT DOCUMENTS

| | | | |
|---|---|---|---|
| DE | 102010030046 A1 | | 2/2011 |
| DE | 202012102250 U1 | | 11/2012 |
| EP | 0038590 A2 | | 10/1981 |
| EP | 2366323 A1 | | 9/2001 |
| EP | 2113605 | | 11/2009 |
| GB | 1372036 A | | 10/1974 |
| GB | WO 2012032283 A1 | * | 3/2012 |
| KR | 20070082389 A | | 8/2007 |
| WO | WO 9705202 | | 12/1997 |
| WO | WO 9705203 | | 12/1997 |
| WO | WO 9749664 | | 12/1997 |
| WO | WO 9832832 | | 7/1998 |
| WO | WO 9832827 | | 9/1998 |
| WO | WO 9859030 A1 | | 12/1998 |
| WO | WO 9914298 | | 3/1999 |
| WO | WO 2006/055787 | | 5/2006 |
| WO | WO 2008/128818 A1 | | 10/2008 |
| WO | WO 2012032283 A1 | | 3/2012 |

OTHER PUBLICATIONS

International Search Report and Written Opinion, dated Mar. 10, 2015, U.S. Appl. No. 14/594,194, 12 pgs.
International Search Report and Written Opinion, dated Mar. 30, 2015, U.S. Appl. No. 14/594,190, 10 pgs.
International Search Report and Written Opinion, dated Mar. 31, 2015, U.S. Appl. No. 14/594,191, 9 pgs.
International Search Report and Written Opinion, dated Apr. 17, 2015, U.S. Appl. No. 14/594,189, 10 pgs.
International Search Report and Written Opinion, dated Apr. 15, 2015, U.S. Appl. No. 14/594,187, 10 pgs.
International Search Report and Written Opinion, dated Mar. 25, 2015, U.S. Appl. No. 14/594,192, 10 pgs.
International Search Report and Written Opinion, dated Mar. 31, 2015, U.S. Appl. No. 14/594,195, 11 pgs.
International Search Report and Written Opinion, dated Mar. 30, 2015, U.S. Appl. No. 14/594,196, 12 pgs.
F. Zaragoza Dorwald, "Side Reactions in Organic Synthesis", 2005, WILEY-VCH Verlag GmbH & Co. KGaA, Weinheim, Preface. p. IX.
Okubayashi et al., Journal of Applied Polymer Science, "Improvement of Wettability of Hydrophobic Films by Impregnation of Anthraquinone Attached to Polyoxyethylene Glycol", 2005, vol. 97, pp. 545-549.
Corrales et al., Journal of Photochemistry and Photobiology A: Chemistry, "Novel water soluble copolymers based on thioxanthone: photochemistry and photoinitiation activity", 2005, 169, pp. 95-100.
Corrales et al., Journal of Photochemistry and Photobiology A: Chemistry, "Free radical macrophotoinitiators: an overview on recent advances", 2003, 159, pp. 103-114.
Allen et al., European Polymer Journal, "Photochemistry of Thioxanthones-III Spectroscopic and Flash Photolysis Study on Hydroxy and Methoxy Derivatives", 1986, vol. 22, No. 9, pp. 691-697.
U.S. Appl. No. 14/594,187, filed Jan. 12, 2015, Alan David Willey et al.
U.S. Appl. No. 14/594,189, filed Jan. 12, 2015, Alan David Willey et al.
U.S. Appl. No. 14/594,191, filed Jan. 12, 2015, Randall Alan Watson et.
U.S. Appl. No. 14/594,192, filed Jan. 12, 2015, Alan David Willey et al.
U.S. Appl. No. 14/594,194, filed Jan. 12, 2015, Alan David Willey et al.
U.S. Appl. No. 14/594,195, filed Jan. 12, 2015, Alan David Willey et al.
U.S. Appl. No. 14/594,196, filed Jan. 12, 2015, Alan David Willey et al.
Akat, H. et al., "Poly(ethyele glycol)-thioxanthone prepared by Diels-Alder click chemistry as one-component polymeric photoinitiator for aqueous free-radical polymerization", Journal of Polymer Science, Part A: Polymer Chemistry, vol. 48, 2109-2114 (2010).

\* cited by examiner

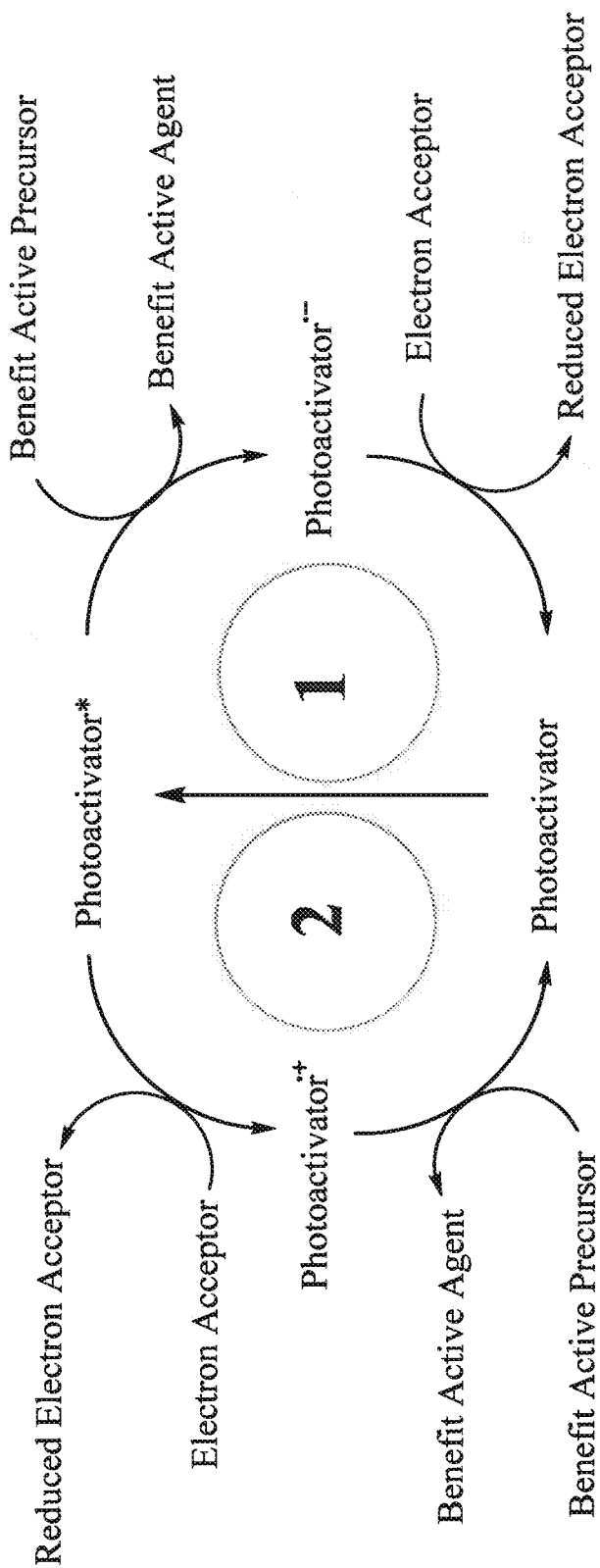

PHOTOACTIVATORS

FIELD OF THE INVENTION

The present invention relates to photoactivators and their use in compositions comprising one or more of the photoactivators to generate one or more benefit active agents, effective as a bleaching agent, stain remover, or antimicrobial and/or in eliminating biofilm. The present invention also relates to methods for cleaning and/or bleaching surfaces, and for providing a method of disinfecting or sanitizing surfaces and/or removing biofilm.

BACKGROUND OF THE INVENTION

Cleaning compositions are used throughout the world in people's homes and workplaces. These compositions range from surface cleaners and disinfectants to bleach for removing stains from one's clothes or teeth. However, conventional cleaning and whitening compositions are limited by the standard chemistry which generates the cleaning or whitening attribute of the composition.

Conventional low cost cleaners, such as chlorine bleach (sodium hypochlorite), are limited in their ability to disinfect and sanitize. For example, such systems have limited benefit on biofilms, a complex biological community formed extensively in the natural environment by bacteria.

Another attempt at eliminating biofilm is through the production of chlorine dioxide and other biocidal gases. Specifically, it is known that chlorine dioxide can be generated by mixing a chlorine dioxide precursor, such as a metal chlorite, and an activator component, such as a transition metal or acid. When each of the components are combined the chlorine dioxide precursor and activator component react to form chlorine dioxide. Such reactions are highly volatile and toxic and are, therefore, not desirable for home applications. Furthermore, these components must be sequestered to prevent premature formation of the chlorine dioxide. However, multi-compartment packaging is more expensive and can still allow premature mixing of the components and accidental generation of chlorine dioxide. As such, such systems are undesirable.

Yet another attempt at eliminating biofilm is through the use of a photoactivator to produce chlorine dioxide. Specifically, it is known to use titanium dioxide ($TiO_2$) and a chlorine dioxide precursor in conjunction with exposure to ultraviolet light to generate chlorine dioxide. However, such processes are undesirable due to the health risks associated with exposure to ultraviolet light, the degradation which can occur to the other components of the cleaning compositions, and the use of an insoluble inorganic photoactivator. In addition, titanium dioxide forms particulates which leave undesirable residue on surfaces and requires additives to suspend in and imparts opaqueness to compositions.

As such, there remains a need for a water-soluble photoactivator that can enable the generation of one or more benefit active agents effective as a bleaching agent, stain remover, or antimicrobial and/or in eliminating biofilm. There further remains a need for a water-soluble photoactivator that produces a substantially colorless consumer product composition that is effective as a bleaching agent, stain remover, or antimicrobial and/or in eliminating biofilm and activatable by visible light.

SUMMARY OF THE INVENTION

The present invention, in one aspect, relates to a photoactivator comprising a photoactive moiety and a hydrophilic moiety. The photoactivator comprises less than about 35%, by weight of the photoactivator, of the photoactive moiety. The photoactivator can be activated to a photo-excited state by excitation with incident radiation of a wavelength between about 350 nm and about 750 nm, preferably between about 350 nm and about 420 nm.

In another aspect, the present invention relates to a photoactivator having the formula:

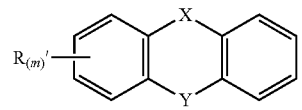

wherein,
X is selected from the group consisting of C, O, NH, C=O, $CH_2$, CHR", CR"R''', S, SO, and $SO_2$;
Y is selected from the group consisting of C, O, NH, C=O, $CH_2$, CHR", CR"R''', S, SO, and $SO_2$;
R', R" and R''' may be —H or selected from a group of substituents that include a moiety selected from the group consisting of Oxygen, Nitrogen, Sulfur, Halogen and Hydrocarbon;
at least one of R', R" or R''' further comprises a hydrophilic moiety R;
R is selected from the group consisting of water soluble oligimers, water soluble polymers and water soluble copolymers;
m is an integer from 0-8; and
the combined molecular weight of the substituents R', R" and R''' is greater than 400 atomic mass units (AMU).

The present invention further relates to the use of the photoactivators of the present invention in consumer product compositions and to methods of cleaning surfaces, bleaching stains, disinfecting surfaces, and removing biofilms.

It has now been surprisingly found that providing a photoactivator according to the present invention enables the generation of one or more benefit active agents effective as a bleaching agent, stain remover, or antimicrobial and/or in eliminating biofilm. It has also now been surprisingly found that providing a photoactivator of the present invention in a consumer product composition, can produce a consumer product composition that is effective as a bleaching agent, stain remover, or antimicrobial and/or in eliminating biofilm.

BRIEF DESCRIPTION OF THE DRAWINGS

The FIGURE is a schematic representing reactions involving the photoactivators of the present invention.

DETAILED DESCRIPTION OF THE INVENTION

The present invention relates to photoactivators comprising a photoactiave moiety and a hydrophilic moiety. Furthermore, the present invention also relates to photocatalyzable consumer product compositions comprising the photoactivator, an electron acceptor and a benefit active precursor. Still further, the present invention also relates to methods for cleaning and/or bleaching surfaces, and for providing a method of disinfecting or sanitizing surfaces and/or eliminating biofilm using the photoactivator, an electron acceptor and a benefit active precursor.

Photoactivator

The water soluble photoactivators of the present invention comprise a photoactive moiety and a hydrophilic moiety. For purposes of the present invention, the term "hydrophilic moiety" refers to a moiety that is attracted to water and dissolves in water to form a homogenous solution. In one embodiment, the hydrophilic moiety is selected from the group consisting of water soluble oligimers, water soluble polymers and water soluble copolymers. In one preferred embodiment, the hydrophilic moiety may be selected from the group consisting of alkylene oxide oligimers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, polysaccharides, 2-ethyl-2-oxazoline, hydroxyethyl methacrylate, vinyl pyridine-N-oxide, diallyl dimethyl ammonium chloride, maleic acid, lysine, arginine, histidine, aspartic acid, glutamic acid, serine, threonine, asparagine, glutamine, isopropyl acrylamide, styrene sulfonic acid, vinyl methyl ether, vinyl phosphoinic acid, ethylene imine, and mixtures thereof. In one especially preferred embodiment, the hydrophilic moiety may be selected from the group consisting of alkylene oxide oligimer polymers, alkylene oxide oligimer copolymers, vinyl alcohol, vinyl pyrrolidone, acrylic acid, acrylamide, cellulose, and mixtures thereof. For purposes of the present invention, the term "photoactive moiety" refers to an organic conjugated moiety that is capable of absorbing a photon of light and thereby forming an excited state (singlet or triplet). It will be understood that the term "photoactive moiety" does not, however, refer to a charge-transfer excited state. It will further be understood that the photoactive moieties, as disclosed herein, may include a single moiety or a combination of two, three, four or any other number of moieties, as known in the art.

In one embodiment of the present invention, the photoactive moiety is selected from the group consisting of 1,1'-biphenyl-4,4'-diamine, 1,1'-biphenyl-4-amine, benzophenone, 1,1'-biphenyl-4,4'-diol, 1,1'-biphenyl-4-amine, 1,1'-biphenyl-4-ol, 1,1':2',1"-terphenyl, 1,1':3',1"-terphenyl, 1,1':4',1":4",1'''-quaterphenyl, 1,1':4',1"-terphenyl, 1,10-phenanthroline, 1,1'-biphenyl, 1,2,3,4-dibenzanthracene, 1,2-benzenedicarbonitrile, 1,3-isobenzofurandione, 1,4-naphthoquinone, 1,5-naphthalenediol, 10H-phenothiazine, 10H-phenoxazine, 10-methylacridone, 1-acetonaphthone, 1-chloroanthraquinone, 1-hydroxyanthraquinone, 1-naphthalenecarbonitrile, 1-naphthalenecarboxaldehyde, 1-naphthalenesulfonic acid, 1-naphthalenol, 2(1H)-quinolinone, 2,2'-biquinoline, 2,3-naphthalenediol, 2,6-dichlorobenzaldehyde, 21H,23H-porphine, 2-aminoanthraquinone, 2-benzoylthiophene, 2-chlorobenzaldehyde, 2-chlorothioxanthone, 2-ethylanthraquinone, 2H-1-benzopyran-2-one, 2-methoxythioxanthone, 2-methyl-1,4-naphthoquinone, 2-methyl-9(10-methyl)-acridinone, 2-methylanthraquinone, 2-methylbenzophenone, 2-naphthalenamine, 2-naphthalenecarboxylic acid, 2-naphthalenol, 2-nitro-9(10-methyl)-acridinone, 9(10-ethyl)-acridinone, 3,6-qcridinediamine, 3,9-dibromoperylene, 3,9-dicyanophenanthrene, 3-benzoylcoumarin, 3-methoxy-9-cyanophenanthrene, 3-methoxythioxanthone, 3'-methylacetophenone, 4,4'-dichlorobenzophenone, 4,4'-dimethoxybenzophenone, 4-bromobenzophenone, 4-chlorobenzophenone, 4'-fluoroacetophenone, 4-methoxybenzophenone, 4'-methylacetophenone, 4-methylbenzaldehyde, 4-methylbenzophenone, 4-phenylbenzophenone, 6-methylchromanone, 7-(diethylamino)coumarin, 7H-benz[de]anthracen-7-one, 7H-benzo[c]xanthen-7-one, 7H-furo[3,2-g][1]benzopyran-7-one, 9(10H)-acridinone, 9(10H)-anthracenone, 9(10-methyl)-acridinone, 9(10-phenyl)-acridinon, 9,10-anthracenedione, 9-acridinamine, 9-cyanophenanthrene, 9-fluorenone, 9H-carbazole, 9H-fluoren-2-amine, 9H-fluorene, 9H-thioxanthen-9-ol, 9H-thioxanthen-9-one, 9H-thioxanthene-2,9-diol, 9H-xanthen-9-one, acetophenone, acridene, acridine, acridone, anthracene, anthraquinone, anthrone, α-tetralone, benz[a]anthracene, benzaldehyde, benzamide, benzo[a]coronene, benzo[a]pyrene, benzo[f]quinoline, benzo[ghi]perylene, benzo[rst]pentaphene, benzophenone, benzoquinone, 2,3,5,6-tetramethyl, chrysene, coronene, dibenz[a,h]anthracene, dibenzo[b,def]chrysene, dibenzo[c,g]phenanthrene, dibenzo[def,mno]chrysene, dibenzo[def,p]chrysene, DL-tryptophan, fluoranthene, fluoren-9-one, fluorenone, isoquinoline, methoxycoumarin, methylacridone, michler's ketone, naphthacene, naphtho[1,2-g]chrysene, N-methylacridone, p-benzoquinone, p-benzoquinone, 2,3,5,6-tetrachloro, pentacene, phenanthrene, phenanthrenequinone, phenanthridine, phenanthro[3,4-c]phenanthrene, phenazine, phenothiazine, p-methoxyacetophenone, pyranthrene, pyrene, quinoline, quinoxaline, riboflavin 5'-(dihydrogen phosphate), thioxanthone, thymidine, xanthen-9-one, xanthone, derivatives thereof, and mixtures thereof.

Preferably, the photoactive moiety is selected from the group consisting of xanthone, xanthene, thioxanthone, thioxanthene, phenothiazine, fluorescein, benzophenone, alloxazine, isoalloxazine, flavin, derivatives thereof, and mixtures thereof. In one preferred embodiment, the photoactive moiety is thioxanthone.

Other suitable water-soluble photoactivators for the consumer product compositions of the present invention include fluoresceins and derivatives thereof; preferably halogen substituted fluoresceins; more preferably bromo- and iodo-fluoresceins such as dibromo fluorescein, diiodo fluorescein, rose bengal, erythrosine, eosin (e.g. Eosin Y).

It is a further aspect of the present invention that the photoactivator preferably comprises less than about 35%, about 30%, about 25%, about 20%, about 15%, about 10%, about 5%, about 3% and about 2%, by weight of the photoactivator, of the photoactive moiety. As such, the photoactivator preferably comprises at least about 65%, about 70%, about 75%, about 80%, about 85%, about 90%, about 95%, about 97%, and about 98%, by weight of the photoactivator, of hydrophilic moiety. In one aspect, the photoactivator comprises less than about 2%, by weight of the photoactivator, of photoactive moiety (such as thioxanthone), and at least about 98%, by weight of the photoactivator, of hydrophilic moiety (such as polyethylene glycol). Without wishing to be bound by theory, it is believed that such a photoactivator not only is water soluble, but will resist aggregation due to the steric hindrance imparted by the hydrophilic moiety or any other non-photoactive moiety.

It is still further another aspect of the present invention that the photoactive moiety has an absorption band between about 350 nm and 750 nm, preferably between about 350 nm and about 420 nm between about 350 nm and about 750 nm, about 350 nm and about 600 nm, about 350 nm and about 420 nm, and about 380 nm and about 400 nm.

In another embodiment, the photoactive moiety does not have an absorption band between about 420 nm and about 720 nm, about 500 and about 700 nm, about 500 nm and about 650 nm, and about 500 nm and about 600 nm. In this embodiment, it will be understood that the photoactivator will be substantially colorless to the human eye when used in an aqueous solution at a concentration of about 500 ppm.

In yet another aspect of the present invention, the photoactivator can be activated to a photo-excited state by excitation with incident radiation of a wavelength greater than 350 nm, preferably between about 350 nm and about 750 nm, more preferably between about 350 nm and about 420 nm. In one embodiment, the photo-excited state lifetime is greater than about 0.5 nanosecond, 1 nanosecond, 10 nanoseconds, 50 nanoseconds, 100 nanoseconds, 300 nanoseconds and 500 nanoseconds. In another embodiment, the photo-excited state of the photoactivator has an energy greater than about 100 kJ/mol, 150 kJ/mol, 200 kJ/mol and 300 kJ/mol more than a ground state of the photoactivator.

In one embodiment, the photoactivator can be excited to a "singlet state" and in another a "triplet state", as both of those terms are known in the art.

In yet another embodiment, the present invention relates to a photoactivator having the formula:

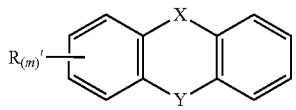

wherein,
X is selected from the group consisting of C, O, NH, C=O, CH$_2$, CHR", CR"R"', S, SO, and SO$_2$;
Y is selected from the group consisting of C, O, NH, C=O, CH$_2$, CHR", CR"R"', S, SO, and SO$_2$;
R', R" and R"' may be —H or selected from a group of substituents that include a moiety selected from the group consisting of Oxygen, Nitrogen, Sulfur, Halogen and Hydrocarbon;
at least one of R', R" or R"' further comprises a hydrophilic moiety R;
R is selected from the group consisting of water soluble oligimers, water soluble polymers and water soluble copolymers;
m is an integer from 0-8; and
the combined molecular weight of the substituents R', R" and R"' is greater than 400 atomic mass units (AMU).

It can be appreciated by one of ordinary skill in the art that the substituent(s) R' as depicted in the formula above reflects that the substitution of the photoactivator may include any number of substituents from zero to eight and that these substituents may be covalently attached to the peripheral carbon atoms of the photoactivator. Where m>1, the multiple R' groups can be independently selected from a group of substituents that include a moiety selected from the group consisting of Oxygen, Nitrogen, Sulfur, Halogen and Hydrocarbon.

In one embodiment, R may be selected from the group consisting of alkylene oxide oligimers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, polysaccharides, 2-ethyl-2-oxazoline, hydroxyethyl methacrylate, vinyl pyridine-N-oxide, diallyl dimethyl ammonium chloride, maleic acid, lysine, arginine, histidine, aspartic acid, glutamic acid, serine, threonine, asparagine, glutamine, isopropyl acrylamide, styrene sulfonic acid, vinyl methyl ether, vinyl phosphoinic acid, ethylene imine, and mixtures thereof.

R', R" and R"' moieties that may replace hydrogen and which contain only carbon and hydrogen atoms include any hydrocarbon moieties, as known in the art, including, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Specific non-limiting examples of such groups are:

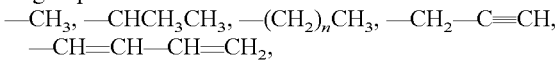

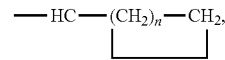

-φCH$_3$, -φCH$_2$φ, -φ, and -φ-φ.

where n is independently chosen as being from 0-22
R', R" and R"' moieties containing oxygen atoms that may replace hydrogen include hydroxy, acyl or keto, ether, epoxy, carboxy, and ester containing groups. Specific non-limiting examples of such oxygen containing groups are:

—CH$_2$OH, —CCH$_3$CH$_3$OH, —CH$_2$COOH, —C(O)—(CH$_2$)$_n$CH$_3$, —C(O)—R, —C(O)—OR, —O(CH$_2$)$_n$CH$_3$, —O—R, =O, —OH, —(CH$_2$)$_n$—O—(CH$_2$)$_n$CH$_3$, —(CH$_2$)$_n$—O—R, —(CH$_2$)$_n$—O—(CH$_2$)$_n$—OH, —(CH$_2$)$_n$COOH, —(CH$_2$)$_n$COOR, -φOH, -φO(CH$_2$)$_n$CH$_3$, φO—R, -φ(CH$_2$)$_n$OH,

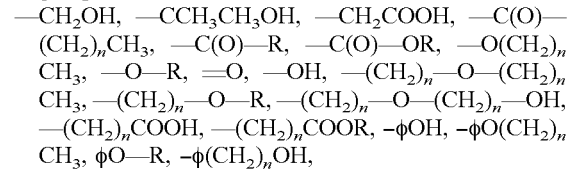

where n is independently chosen as being from 0-22
R', R" and R"' moieties containing sulfur atoms that may replace hydrogen include the sulfur-containing acids and acid ester groups, thioether groups, mercapto groups and thioketo groups. Specific non-limiting examples of such sulfur containing groups are:

—S(CH$_2$)$_n$CH$_3$, —(CH$_2$)$_n$S(CH$_2$)$_n$CH$_3$, —SO$_3$(CH$_2$)$_n$CH$_3$, SO$_2$(CH$_2$)$_n$CH$_3$, —(CH$_2$)$_n$COSH, —SH, —(CH$_2$)$_n$SCO, —(CH$_2$)$_n$C(S)(CH$_2$)$_n$CH$_3$, —SO$_3$H, —O(CH$_2$)$_n$C(S)CH$_3$, —S—R, —(CH$_2$)$_n$S—R, —SO$_3$—R, —SO$_2$—R, —(CH$_2$)$_n$COS—R, —(CH$_2$)$_n$C(S)—R, —O(CH$_2$)$_n$C(S)—R, =S, and

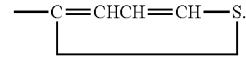

where n is independently chosen as being from 0-22
R', R" and R"' moieties containing nitrogen atoms that may replace hydrogen include amino groups, the nitro group, azo groups, ammonium groups, amide groups, azido groups, isocyanate groups, cyano groups and nitrile groups. Specific non-limiting examples of such nitrogen containing groups are:

—NH$_2$, —NH$_3^+$, —NH(CH$_2$)$_n$CH$_3$, —N((CH$_2$)$_n$CH$_3$)$_2$, —(CH$_2$)$_n$NH(CH$_2$)$_n$CH$_3$, —(CH$_2$)$_n$N((CH$_2$)$_n$CH$_3$)$_2$, —CH$_2$CONH$_2$, —CH$_2$CONH(CH$_2$)$_n$CH$_3$, —CH$_2$CON((CH$_2$)$_n$CH$_3$)$_2$, —NRH$_2^+$, —NH—R, —NR$_2$, —(CH$_2$)$_n$NH—R, —(CH$_2$)$_n$NR$_2$, —(CH$_2$)$_n$CONH—R, —(CH$_2$)$_n$CONR$_2$, —(CH$_2$)$_n$CON$_3$, —(CH$_2$)$_n$CH=NOH, —CN, —CH(CH$_2$)$_n$NCO, —(CH$_2$)$_n$NCO, —Nφ, —φN=NφOH, and =N.

where n is independently chosen as being from 0-22.
R', R" and R"' moieties containing halogen atoms that may replace hydrogen include chloro, bromo, fluoro, iodo groups and any of the moieties previously described where a hydrogen or a pendant alkyl group is substituted by a halo group to form a stable substituted moiety. Specific non-limiting examples of such halogen containing groups are: —Cl, —Br, —I, —(CH$_2$)$_n$COCl, —$\phi$F$_5$, —$\phi$Cl, —CF$_3$, and —(CH$_2$)$_n$$\phi$Br.

It is understood that any of the above moieties that may replace hydrogen can be substituted into each other in either a monovalent substitution or by loss of hydrogen in a polyvalent substitution to form another monovalent moiety that can replace hydrogen in the organic compound or radical.

As used herein "$\phi$" represents a phenyl ring.

Photocatalyzable Composition

The present invention also relates to photocatalyzable compositions, such as consumer product compositions, that include the photoactivator, as described in further detail above, an electron acceptor and a benefit active precursor. As used herein, consumer product compositions encompass beauty care compositions, fabric and home care compositions, and health care compositions. Beauty care compositions generally include compositions for treating hair, including, bleaching, coloring, dyeing, conditioning, growing, removing, retarding growth, shampooing, styling; deodorants and antiperspirants; personal cleansing; color cosmetics; products, and/or methods relating to treating skin, including application of creams, lotions, and other topically applied products for consumer use; and products and/or methods relating to orally administered materials for enhancing the appearance of hair, skin, and/or nails; and shaving. Fabric and home care compositions generally include compositions for treating fabrics, hard surfaces and any other surfaces in the area of fabric and home care, such as car care, dishwashing, fabric conditioning (including softening), laundry detergency, laundry and rinse additive and/or care, hard surface cleaning and/or treatment, and other cleaning for consumer or institutional use. Oral care compositions generally include compositions for use with any soft and/or hard tissue of the oral cavity or conditions associated therewith, e.g., anti-caries compositions, anti-microbial compositions, anti-plaque chewing gum, compositions, breath compositions, confectionaries, dentifrices/toothpastes, denture compositions, lozenges, rinses, and tooth whitening compositions.

The photocatalyzable consumer product composition may be an aqueous solution, a solid, or incorporated into a material, such as a film. In another embodiment, the individual components of the photocatalyzable consumer product composition may be incorporated into both an aqueous solution and a material, such as a film. In one embodiment, the photoactivator may be included in a film and the electron acceptor and/or benefit active precursor maybe included in an aqueous solution. It will be understood that in this particular embodiment, a film comprising a photoactivator may be applied to surface and an aqueous solution comprising an electron acceptor and benefit active precursor may be applied separately.

However, if the photocatalyzable consumer product composition is an aqueous composition, the composition may comprise from 1% to 99%, by weight of the composition, of water. It will therefore be understood that the photocatalyzable consumer product composition can be in concentrated or diluted form. It is further contemplated that all or a portion of the water may be replaced with another solvent such as ethanol, glycol, glycol-ethers, glycerin, water soluble acetates and alcohols.

As noted above, the present invention relates to photocatalyzable consumer product compositions that include the photoactivator, an electron acceptor and a benefit active precursor. In such embodiments it will be understood that the photocatalyst can be excited into a singlet and/or triplet state via activation by light in the visible wavelengths. It will also be understood that the benefit active precursor can be converted into a benefit active agent upon triggering by the photocatalyst in an activated singlet and/or triplet state after exposure to visible light. It will be understood that the photocatalyst is unreactive with the benefit active precursor without activation by light.

The photocatalyzable consumer product composition is a system responsive to light; for example, visible, ultraviolet and/or infrared. In one preferred embodiment, the system is responsive visible light. In the present embodiment, photon transfer from the light source to the photocatalyst allows the reaction to progress to create an effective benefit agent that, in some embodiments, may act to clean, disinfect or sanitize, and/or bleach or whiten.

Electron Acceptor

The photocatalyzable consumer product composition of the present invention comprises an electron acceptor. It will be understood to those skilled in the art that photocatalytic reduction and oxidation chemistries differ from conventional, energy-transfer photochemistry in that the photocatalytically-induced transfer of electrons can result in chemical transformation of reagents (e.g. transformation of the benefit precursor material to the benefit active) and oxidation of the benefit precursor material to produce a benefit active which is capable of providing a beneficial result, for example, cleaning, disinfection, bleaching, and/or whitening.

For the purposes of the present invention the term "electron acceptor" is defined as "a compound or moiety which accepts an electron from the photoactivator when the photoactivator is in a photo-excited state and/or one electron reduced state." This electron transfer process is normally a very rapid and reversible process.

The ability of the electron acceptor to accept an electron from the excited photoactivator is generally described in Turro, N.J., V. Ramamurthy, and J. C. Scaiano, *Principles of Molecular Photochemistry: An Introduction*, Chapter 7, p. 41 (University Science Books 2009, Paperback edition). It is understood that the reaction between the reactants is favored when the Gibbs free energy (delta G) is less than 0.

The reaction process is exemplified schematically in the FIGURE. As shown in the FIGURE, Reaction 1 (the right half of the FIGURE) illustrates a reaction in which electron transfer occurs from a benefit acative precursor to the excited state of the photoactivator (thereby forming a benefit active) and then from the one-electron reduced form of the photoactivator to the electron acceptor as described herein. As shown in the FIGURE, Reaction 2 (the left half of the FIGURE) illustrates a reaction in which electron transfer occurs from the excited state of the photoactivator to the electron acceptor and then from the one electron oxidized form of the photoactivator to the benefit active precursor (thereby forming a benefit active). In all cases, the Gibbs free energy for the electron transfer should be less than 0. It is understood that the conversion of the photoactivator to its photoactivated state ("Photoactivator*") is initiated by the absorption of light, which is also present in the reaction.

It will further be understood to those skilled in the art that any electron transfer between species comprising the photocatalyzable consumer product composition further requires effective Brownian collision to occur between the reacting species and that effective electron transfer between the photochemically excited state of the photoactivator and any species comprising the photocatalyzable consumer product composition (e.g. the electron acceptor) may further depend on the lifetime of the excited state of the photoactivator, the concentration of the photoactivator, and the concentration of the electron acceptor.

The electron acceptor of the present invention may be any species that accepts an electron from the photoactivator when the photoactivator is in a photo-excited state and/or reduced state. The electron acceptor must be present in the photocatalyzable consumer product composition in sufficient concentration to enable Brownian collisions with the photoactivator, given the concentration of the photoactivator and the lifetime of the photochemically excited state of the photoactivator.

A suitable electron acceptor acceptor can be selected from the group consisting of:

Viologens: e.g., methyl viologen;
Biyridiums: e.g., 2,2' bipyridinium, 3,3' bipyridinium, 3,4' bipyridinium;
Quinones: e.g., para-Benzoquinone, 2,3-Dichloro-5,6-dicyano-p-benzoquinone, Tetrahydroxy-1,4-quinone hydrate, 2,5-di-tert-butylhydroquinone, tert-Butylhydroquinone, Anthraquinone, Diaminoanthroquinone, Anthraquinone-2-sulfonic acid;
Polycyclic aromatic hydrocarbons: e.g., Naphthalene, Anthracene, Pyrene, Dicyanobenzene, dicyano naphthalene, dicyano anthracene, dicyanopyrene;
Transition metal salts: e.g., Chloropentaamine cobalt dichloride, Silver nitrate, Iron Sulfate, copper sulfate;
Nanoparticle semiconductors: e.g., Titanium Dioxide, Zinc Oxide, Cadmium Selenide;
Persulfates: e.g., Ammonium persulfate, Sodium persulfate, Potassium persulfate;
Nitroxyl radicals: e.g., (2,2,6,6-Tetramethylpiperidin-1-yl)oxy, Dimethylthiourea, Tetranitromethane, Lithium, sodium and potassium acetoacetate, Oxaloacetic acid;
Ascorbic acid salts: e.g., Sodium ascorbate;
Phenols: 2,6-Dicholorophenolindophenol, 4-methoxyphenol;
Others: 4-Methylmorpholine N-oxide, 4-tert-Butylcatechol, Allopurinol, Pyridoxal 5'-phosphate, pyridoxal hydrochloride, Sodium benzoate, Sodium Nitrate, Sodium Nitrite, Diatomic Oxygen; and
Mixtures thereof.

With respect to suitable electron acceptors, diatomic oxygen is an electron acceptor which can be present in the composition due to dissolution of oxygen from the atmosphere into the composition, especially in an aqueous liquid composition. Most aqueous liquid compositions will have a sufficient content of diatomic oxygen as an electron acceptor to enable the electron transfer process. This can be enhanced with the addition of other electron acceptors in the composition as an ingredient. With respect to solid compositions (or other substantially anhydrous compositions), such compositions typically will not have a sufficient level of diatomic oxygen to enable the electron transfer process. Therefore, a solid composition which does not contain an electron acceptor as an added ingredient to the composition can nonetheless be photochemically active upon dissolution of the solid composition into an aqueous solution due to the presence of diatomic oxygen in the aqueous solution (e.g. a solid detergent composition that is dissolved in water can form an aqueous solution containing diatomic oxygen at a level sufficient to enable the electron transfer process). The present invention therefore encompasses a solid composition comprising a water soluble photoactivator and an oxyhalite, without an electron acceptor being added to the composition as an ingredient. Such a solid composition can be photoactivated upon dissolution in water wherein diatomic oxygen can serve as the electron acceptor.

With respect to suitable electron acceptors, nanoparticle semiconductors such as titanium dioxide can be used at relatively low levels to serve as electron acceptors, preferably less than about 1%, preferably less than 0.5%, preferably less than 0.1%, preferably less than 0.05%, preferably less than 0.01%, by weight of the consumer product composition. At higher levels, such materials may function efficiently as photoactivators, however any use of nanoparticle semiconductors in the present invention is preferably at a low enough level such that the material does not function efficiently as a photoactivator to provide significant consumer noticeable benefits and functions instead as an electron acceptor.

The photocatalyzable consumer product composition is preferably an aqueous composition and the electron acceptor is preferably a water soluble species selected from one or more of the groups listed above.

Benefit Active Precursor

The photocatalyzable consumer product composition of the present invention comprises a benefit active precursor. When used in the photocatalyzable consumer product composition of the present invention and exposed to appropriate light (such as in the methods of the present invention), the benefit active precursor is converted into a benefit active (such as chlorine dioxide). The benefit active is the one electron oxidation product(s) of the benefit active precursor.

In one aspect of the present invention, the benefit active precursor is a material selected from one or more species according to the following formula:

$$A[XO_n]_m$$

wherein

A is selected from the group consisting of monovalent cations, divalent cations, and trivalent cations; A can be an organic or inorganic cation; A is preferably selected from the group consisting of Aluminum, Barium, Calcium, Cobalt, Chromium, Copper, Iron, Lithium, Potassium, Rubidium, Magnesium, Manganese, Molybdenum, Nickel, Sodium, Titanium, Vanadium, Zinc, ammonium, alkyl-ammonium, aryl-ammonium, and mixtures thereof; A is more preferably selected from the group consisting of lithium, sodium, potassium, magnesium, calcium, ammonium, and mixtures thereof;

X is selected from the group consisting of chlorine, bromine, iodine, and mixtures thereof;

n is 1, 2, 3, or 4, preferably n is 2, 3, or 4; and m is 1, 2, or 3.

The benefit active precursor of the present invention is preferably an oxyhalite, and is preferably selected from the group consisting of hypochlorite salts, chlorite salts, chlorate salts, perchlorate salts, hypobromite salts, bromite salts, bromate salts, perbromate salts, hypoiodate salts, iodite salts, iodate salts, periodate salts and mixtures thereof. Suitable benefit active precursors include those selected from the group consisting of sodium chlorite, sodium bromite, sodium iodite, potassium chlorite, potassium bromite, potassium iodite, sodium chlorate, sodium bromate, sodium iodate, potassium chlorate, potassium bromate, potassium iodate, sodium hypochlorite, sodium hypobromite, sodium hypoiodite, sodium perchlorate, potassium perchlorate, and mixtures thereof. In at least one aspect, the benefit active precursor is not a hypo-halite, such as hypochlorite.

In one aspect, the benefit active precursor may be a chlorite salt. A specific example of a chlorite salt suitable for use as a benefit active precursor is sodium chlorite (NaClO$_2$). In this embodiment, activation of the chlorite salt through transfer of an electron to the photoactivated photocatalyst results in the formation of the benefit active chlorine dioxide (ClO$_2$). Chlorine dioxide is a potent biocide and bleaching agent. In addition to salts, various other precursor forms are contemplated herein.

Optional Additives

The photocatalyzable consumer product compositions of the invention may also contain additional adjunct additives. The precise nature of these additional components and levels of incorporation thereof will depend on the physical form of the composition, and the precise nature of the cleaning, disinfecting and/or whitening operation for which it is to be used. It will be understood that some of the adjunct additives noted below will have photoactive and/or electron acceptor properties, but it will be further understood that such additives will not replace the components noted above.

Suitable photocatalyzable consumer product compositions, and adjunct additives therefor, are described in detail in U.S. application Ser. No. 61/930,993, filed Jan. 24, 2014, entitled "CONSUMER PRODUCT COMPOSITIONS".

Methods of Use

The present invention further relates to methods of using the photoactivators of the present invention in compositions to provide benefits such as cleaning surfaces, bleaching stains (including whitening teeth) disinfecting and/or sanitizing surfaces, removing biofilm from surfaces, and the like.

As such, the present invention encompasses a method of cleaning a surface, the method comprising the steps of contacting the surface with a composition comprising the photoactivator of the present invention and exposing the composition to light, preferably having a wavelength greater than about 350 nm. The light utilized can be from a natural or artificial source.

The present invention further encompasses a method of bleaching a stain, the method comprising the steps of contacting the stain with a composition comprising the photoactivator of the present invention and exposing the composition to light, preferably having a wavelength greater than about 350 nm.

The present invention further encompasses a method of disinfecting a surface, the method comprising the steps of contacting the surface with a composition comprising the photoactivator of the present invention and exposing the composition to light, preferably having a wavelength greater than about 350 nm.

The present invention further encompasses a method of removing biofilm from a surface, the method comprising the steps of contacting the biofilm with a composition comprising the photoactivator of the present invention and exposing the composition to light, preferably having a wavelength greater than about 350 nm.

The present invention also relates to a method for cleaning a stained fabric comprising contacting a stained fabric in need of cleaning with a composition comprising the photoactivator, described in detail above, having at least 0.001 ppm of a photoactivator, described in detail above, followed by exposing the surface of the treated fabric to a source of light having a minimal wavelength range of greater than about 300 nanometers, preferably greater than about 350 nanometers, preferably greater than about 400 nm, up to about 550 nanometers, preferably up to about 500 nanometers.

The present invention further relates to a method for cleaning a surface comprising contacting a surface in need of cleaning with a composition comprising the photoactivator of the present invention, described in detail above, having at least 0.001 ppm of a photoactivator, described in detail above, followed by exposing the surface to a source of light having a minimal wavelength range of greater than about 300 nanometers, preferably greater than about 350 nanometers, up to about 550 nanometers, preferably up to about 500 nanometers.

The present invention further relates to a method for treating or cleaning oral cavity, including teeth or dentures (inside or outside the oral cavity), comprising contacting the oral cavity (including teeth or dentures) in need of treatment or cleaning with a composition comprising the photoactivator of the present invention, described in detail above, having at least 0.001 ppm of a photoactivator, described in detail above, followed by exposing the teeth or dentures to a source of light having a minimal wavelength range of greater than about 300 nanometers, preferably greater than about 350 nanometers, up to about 550 nanometers, preferably up to about 500 nanometers.

Packaging

The compositions comprising the photoactivator of the present invention may be packed in any suitable packaging for delivering the compositions for use. It will be understood, however, that the package may be structured to prevent the photoactivator from absorbing light and, therefore, activation of the benefit active before use. In one aspect, the package can be opaque. In another aspect, the package can be a transparent or translucent package made of glass or plastic so that consumers can see the compositions throughout the packaging. In another aspect, the package may include one or more windows which may be opened to allow the consumer to see the composition and/or activate the composition prior to use and subsequently closed to prevent the photoactivator from absorbing light during storage. In one preferred aspect, the package may be comprised of polyethylene terephthalate, high-density polyethylene, low-density polyethylene, or combinations thereof. Furthermore, preferably, the package may be dosed through a cap at the top of the package such that the composition exits the bottle through an opening in the cap. In one aspect, the opening in the cap may also contain a screen to help facilitate dosing.

Chlorite Quenching Test Method

The photoactivators of the present invention are evaluated for suitability by the following process.

A suitable wavelength for excitation of the photoactivator is determined by recording a UV/Vis spectrum on any suitable UV/Vis spectrophotometer and identifying an absorption band in the range from 350 nm to 750 nm.

The steady state fluorescence is first determined using a Fluorolog 3 (model number FL3-22) fluorescence spectrophotometer from Horiba Jobin Yvon to acquire the fluorescence spectrum of the photoactivator. It will be understood by those skilled in the art that the fluorescence produced by the activator varies depending on the fluorescence quantum yield for the structure. The photoactivators are screened through a wide range of concentrations (1 ppm-10,000 ppm) to determine the concentration which produces the approximate maximum steady state fluorescence.

Fluorescence quenching is demonstrated by producing solutions of the photoactivator at the concentration determined as described above with a range of concentrations of sodium chlorite (1000 ppm-100,000 ppm).

Photoactivators of the present invention are considered suitable if steady state fluorescence is reduced at least 10% (based on counts per second) when the photoactivator is dissolved in a 1% solution of sodium chlorite.

Indigo Carmine Bleaching Test Method

Photoactivators that demonstrate reduced steady state fluorescence in the presence of chlorite are evaluated for the generation of the benefit active chlorine dioxide. A solution of the activator (at the above described concentration) is prepared in 1% aqueous sodium chlorite containing 20 ppm indigo carmine as a bleaching indicator.

The solution is exposed to light at the excitation wavelength for the generation of the excited state of the photoactivator and a UV/Vis spectra taken after ten minutes of light exposure. The reduction in the intensity of the indigo carmine visible absorption peak is used to determine the bleaching efficacy of the photoactivator in the presence of sodium chlorite. Photoactivators of the present invention are considered suitable if the Indigo carmine absorption peak intensity was reduced by more than a control solution that does not contain chlorite.

EXAMPLES

Photoactivator Examples

The following are non-limiting examples of various water soluble organic photoactivators, and syntheses thereof, of the present invention.

9-Oxo-9H-thioxanthene-2-carboxylic acid chloride

A dry 500 mL 1-neck recovery flask containing 13.25 g of 9-oxo-9H-thioxanthene-2-carboxylic acid and a magnetic stir bar is fitted with a dry condenser connected to Firestone valve (with the bubbler exit going through water to trap evolved HCl). After adding 250 mL of thionyl chloride the system is vacuum/nitrogen cycled 5 times and left under positive nitrogen pressure (suspended solid). After refluxing for 5 hours thionyl chloride is removed in vacuo using a rotary evaporator at 60° C. The residual solid on the flask walls is scraped down and broken up and placed under vacuum overnight (0.3 mm Hg) at room temperature. The vacuum is broken while introducing argon and the solid is broken up using a glass rod and spatula while maintaining a flow of argon over the mouth of the flask. The overnight vacuum treatment is repeated leading to 11.92 g of pinkish solid acid chloride.

Thioxanthenone-PEG(10,000) Ester Conjugate

Using oven-dried glassware 434.0 g poly(ethylene glycol) (MW 10,000) is placed in a 3 L 3-neck round-bottom flask with mechanical stirrer, condenser (topped with nitrogen/vacuum inlet), and a Teflon thermocouple connected to temperature controller and heating mantle. The system is cycled between nitrogen and vacuum and left under nitrogen.

The addition of 0.64 g of 4-(dimethylamino)pyridine and 6.3 mL of triethylamine is followed by the addition of 500 mL of anhydrous methylene chloride. The system is cycled between nitrogen and vacuum and left under nitrogen again as the mixture is stirred to dissolve the materials. A suspension of 11.92 g 9-oxo-9H-thioxanthene-2-carboxylic acid chloride in 1160 mL of anhydrous methylene chloride is transferred into the reaction mixture. The system is cycled between nitrogen and vacuum and left under nitrogen again as the pink solid suspension mixture soon became opaque and tan. After stirring at ambient for 3 hours the mixture is stirred an additional 48 hours at 40° C. The reaction mixture is extracted twice with 100 mL of a pH 3 aqueous solution (prepared by mixing 2 parts of saturated aqueous sodium chloride and 1 part water and adjusting the pH with 0.1 N hydrochloride acid). The resulting emulsions required about an hour to separate. After washing the organic phase with 300 mL of saturated aqueous sodium chloride solution it is dried over 300 g of sodium sulfate overnight. After suction filtering the solvent is removed in vacuo using a rotary evaporator to give 379.9 g of yellowish solid which is scraped from the flask and ground up with a mortar and pestle. The ground up solid is placed under 0.18 mm Hg of vacuum overnight before mixing with 1600 mL of water. This cloudy solution is suction filtered through two glass fiber pads to give 1817.2 g of a yellow-green aqueous solution found to be 19.0 weight percent solids after freeze-drying a portion of it. The resulting photoactivator exhibits a suitable excitation wavelength of about 380 nm and comprises about 2%, by weight of the photoactivator, of photoactive moiety.

Anthraquinone-mPEG(550) Ester Conjugate

A 100 mL round-bottom flask containing 5.08 g of poly(ethylene glycol) methyl ether (mPEG-550; $M_n$ ca 550, $T_m$=20° C.), 0.113 g of 4-(dimethylamino)pyridine, 1.4 mL of triethylamine, 40 mL of methylene chloride, and a magnetic stir bar is fitted with a condenser connected to a Firestone valve (for vacuum and nitrogen introduction). While stirring under nitrogen 2.50 g anthraquinone-2-carbonyl chloride is added at room temperature and then the mixture is heated to reflux for 48 hours. After cooling and adding an additional 50 mL of methylene chloride the mixture is extracted with 50 mL of 1M HCl and twice with 50 mL of water. The organic solution is dried over magnesium sulfate. After suction filtering the solvent is removed in vacuo at 45° C. using a rotary evaporator. The light beige solid residue is taken up in 115 mL of water to provide a turbid solution which is suction filtered through a glass fiber pad under a paper filter pad. Freeze-drying led to 4.1 g of a sticky beige solid which is dissolved to make a 10 wt. % aqueous solution. The resulting photoactivator exhibits a suitable excitation wavelength of about 450 nm and comprises about 27%, by weight of the photoactivator, of photoactive moiety.

Anthraquinone-mPEG(2000) Ester Conjugate

A 100 mL round-bottom flask containing 18.47 g of poly(ethylene glycol) methyl ether (mPEG-2000, 1.500 g; $M_n$ ca 2000, $T_m$=52° C.), 0.112 g of 4-(dimethylamino)pyridine, 1.4 mL of triethylamine, 105 mL of methylene chloride, and a magnetic stir bar is fitted with a condenser connected to a Firestone valve (for vacuum and nitrogen introduction). While stiffing under nitrogen 2.50 g anthraquinone-2-carbonyl chloride is added at room temperature and then the mixture is heated to reflux for 48 hours. After cooling and adding an additional 50 mL of methylene chloride the mixture is extracted with 50 mL of 1M HCl and twice with 50 mL of water. The organic solution is dried over magnesium sulfate. After suction filtering the solvent is removed in vacuo at 45° C. using a rotary evaporator. The light beige solid (16.66 g) residue is taken up in 666 mL of water to provide a turbid solution which is suction filtered through a glass fiber pad under a paper filter pad. Freeze-drying led to 12.75 g of a light yellow solid which is dissolved to make a 10 wt. % aqueous solution. The resulting photoactivator exhibits a suitable excitation wavelength of about 435 nm and comprises about 9%, by weight of the photoactivator, of photoactive moiety.

Gantrez-Naphthylmethyl Amide Conjugate

A 250 mL round-bottom flask containing 5.075 g of Gantrez (anhydride form; $M_w$ 216,000; $M_n$ 80,000), 125 mL of tetrahydrofuran, and a magnetic stir bar is fitted with a condenser connected to a Firestone valve (for vacuum and nitrogen introduction) then stirred and heated to reflux under nitrogen. The polymer partially dissolved. After cooling to room temperature 1.32 g of triethylamine is added leading to some solids coming out of solution with the development of a light purple color. The addition of 1.02 g of 1-naphthylenemethylamine led to a darker purple color and the mixture is stirred at room temperature under nitrogen for 26 hours. An aqueous solution of 1.0 N sodium hydroxide (58.5 mL) is slowly added to reaction and the mixture is stirred another 17 hours at room temperature. The two-phase mixture is transferred to a 1 L flask with 100 mL of water and concentrated at 50° C. in vacuo using a rotary evaporator. Three additional cycles were performed adding 100 mL of water and concentrating to give 5.22 g of a tan/yellow solid. This residue is taken up in 105 mL of water, suction filtered, and the filtrate is freeze-dried to provide 7.41 g of a light solid which is diluted to a 5 wt % aqueous solution. The resulting photoactivator exhibits a suitable excitation wavelength of about 405 nm and comprises about 11%, by weight of the photoactivator, of photoactive moiety.

2-(2-Aminoethyl)-1H-benzo[de]isoquinoline-1,3(2H)-dione

A 100 mL round-bottom flask is charged with 20 mL of ethylene diamine along with a magnetic stir bar. A slurry of 5.00 g of 1,8-naphthalic anhydride and 30 mL of pyridine is added to the ethylene diamine, the flask is fitted with an air condenser, and the resulting slurry is stirred and heated to 60° C. under an argon atmosphere for 23 hours and an additional 24 hours at room temperature. The reaction mixture is then poured into 350 mL of water stirring in 1 L beaker and the resulting solid is suction filtered through #4 filter paper and washed with 3×40 mL of water on the funnel. The filtered solid is dried under vacuum (0.3 mm Hg) for 6 hours to give 3.767 g of an off-white powder, 2-(2-aminoethyl)-1H-benzo[de]isoquinoline-1,3(2H)-dione.

Gantrez-Naphthylene Amide Conjugate

A 500 mL round-bottom flask containing 3.00 g of Gantrez (anhydride form; $M_w$ 216,000; $M_n$ 80,000), 75 mL of tetrahydrofuran, and a magnetic stir bar is fitted with an air condenser connected to a Firestone valve (for vacuum and nitrogen introduction) then stirred and heated to 60° C. under argon. The polymer dissolved to give a homogeneous solution. After cooling to room temperature 1.1 mL of triethylamine is added leading to some solids coming out of solution with the development of a reddish color. After cooling to room temperature 0.924 g of 2-(2-aminoethyl)-1H-benzo[de]isoquinoline-1,3(2H)-dione is added, the system is purged with argon again, and then stirred at 60° C. for 20 hours. The freely stirring purple solution with some suspended solids is cooled to room temperature and 35 mL of 1.0 N NaOH is added leading to the precipitation of a gummy, brown material. After 2.5 hours at room temperature 50 mL of methanol is added and stirring is continued at room temperature under argon overnight. The mixture with the insoluble gummy material is then heated to a gentle reflux for 4 hours before concentrating in vacuo using a rotary evaporator at 55° C. After the addition 200 mL of water and subsequent concentration the residue is agitated with 300 mL of water at 55° C. Most of the residue dissolved and the hazy solution is suction filtered while warm on a 90 mm Buchner funnel through layers of #4 filter paper/glass fiber pad/#4 filter paper resulting in a clear (tannish) solution. Freeze-drying led to 6.0 g of an off-white foam which is dissolved in water to make a 0.026 g/mL solution.

1-Naphthoyl-4-mPEG Semicarbazide Conjugate

Methoxypoly(ethylene glycol) isocyanate (1.025 g; MW-2000) is placed in a 10 mL round-bottom flask with a magnetic stir bar and dissolved in 2 mL of methylene chloride. While stirring a suspension of 0.186 g of 1-naphthoic hydrazide in 2 mL of methylene chloride is added, the flask is capped and covered with foil to protect from light, and stirring is continued at room temperature. After 6 days solvent is removed in vacuo using a rotary evaporator to give 1.90 g of white solid. This material is dissolved/suspended in 100 mL of water. This solution is filtered through #3 filter paper to clarify and freeze-dried to provide 1.09 g of fluffy white solid with a pinkish tint. This material is redissolved in a total volume of 100 mL of water to give a 0.0107 g/mL aqueous solution.

Naphthylenemethyl-mPEG(2000) Urea Conjugate

Methoxypoly(ethylene glycol) isocyanate (1.025 g; MW~2000) is placed in a 10 mL round-bottom flask with a magnetic stir bar and dissolved in 2 mL of methylene chloride. While stirring 0.184 g of 1-naphthylenemethylamine is added, the flask is capped and covered with foil to protect from light, and stirring is continued at room temperature. After 4 days solvent is removed in vacuo using a rotary evaporator to give 1.12 g of white solid. This material is dissolved in 50 mL of water to make a hazy homogenous solution (pH 7). This solution is filtered through #3 filter paper to clarify, and then diluted with water to a total volume of 70 mL. A portion of the solution is freeze-dried to determine that the solution had a concentration of 0.0133 g/mL.

Starch-Naphthalene Carbamate Conjugate

A solution of 0.676 g of 1-naphthyl isocyanate in 13 mL of THF is added to 3.24 g of starch (Aldrich catalog number 85652) in a 100 mL round-bottom flask with a magnetic stir bar. The flask is fitted with an air condenser and heated to 60° C. for 3 days under argon. The mixture is concentrated under reduced pressure (rotary evaporator) at 40° C., slurried in 100 mL of water, concentrated again, and repeated. The resulting residue is slurried in 300 mL of water, heated on a steam bath, then centrifuged to separate from most of the solids. The aqueous solution is then suction filtered and freeze-dried to give 0.70 g of white, fibrous solid. A in 0.307 g portion of this solid is suspended in 300 mL of water (with steam heating), let cool to room temperature, then let sit overnight to let solids settle out. The aqueous solution is then suction filtered and diluted to 300 mL. A portion of this solution is freeze-dried to determine that the solution had a concentration of 0.00083 g/mL. The resulting photoactivator exhibits a suitable excitation wavelength of about 330 nm.

mPEG(2000)-Naphthalic Anhydride Conjugate

Solid reagents, 0.300 g of 1,8-naphthalic anhydride and 3.90 g of poly(ethylene glycol) methyl ether (mPEG-2000, 1.500 g; $M_n$ ca 2000, $T_m$=52° C.), were dry-mixed in a 100 mL round-bottom flask contained a magnetic stir bar under argon. Heating the flask to for 24 hours led to a partially fluid suspension of stirring solids. The contents were heated an additional 15 hours at 150° C. before cooling. The solid mass is broken up and dissolve/suspended in 100 mL of water. The fine suspension of solids is suction filtered through a glass fiber pad on a #4 filter paper pad and freeze-dried to give 3.0 g of solid which is diluted with water to make a 0.067 g/mL solution. The resulting photoactivator exhibits a suitable excitation wavelength of about 380 nm and comprises about 9%, by weight of the photoactivator, of photoactive moiety.

Poly(Vinyl Alcohol)-Naphthalene Carbamate Conjugate

Weighed out 1.38 g of poly(vinyl alcohol) (40% hydrolyzed; MW 72,000) in 25 mL flask with a magnetic stir bar. Added 14 mL of tetrahydrofuran (THF) to swell/suspend the polymer. Added 0.338 g of 1-naphthyl isocyanate in 1 mL of THF, placed under an argon atmosphere, covered with foil to shield from light, and stirred at room temperature for 4 days. The viscous slurry is transferred into 60 mL of methanol and stirred as 20 mL of aqueous 1.0 N sodium hydroxide is added. After 23 hours of stirring at room temperature the mixture is transferred into a 1 L flask, fitted with an air condenser and stirred at 60° C. under argon for 16 hours. The mixture is concentrated under reduced pressure (rotary evaporator) at 50° C., slurried again in 200 mL of water (solution pH 11) and concentrated again. The resulting residue is slurried in 150 mL of water and suction filtered to give a clear, yellowish solution. After freeze-drying 1.685 g of fluffy white powder is obtained and diluted with water to a 0.164 g/mL solution. The resulting photoactivator exhibits a suitable excitation wavelength of about 330 nm and comprises about 19%, by weight of the photoactivator, of photoactive moiety.

Benzophenone-mPEG(2000) Carbamate Conjugate

4-Isocyanatobenzophenone (0.138 g) and poly(ethylene glycol) methyl ether (mPEG-2000, 1.500 g; $M_n$ ca 2000, $T_m$=52° C.) were combined in a 10 mL flask with a magnetic stir bar under an argon atmosphere. The mixture is placed in a 80° C. oil bath and stirred as the mixture melted to provide a peach-colored slurry. After stirring for 17.5 hours the mixture is cooled to room temperature to form a solid mass which is partially dissolved in 140 mL of water. After suction filtering through a glass fiber pad on top of a #4 paper pad a clear aqueous solution is attained. Freeze-drying this solution led to 1.53 g of a fluffy white solid. This solid is diluted with water to provide a 0.0263 g/mL solution. The resulting photoactivator exhibits a suitable excitation wavelength of about 425 nm and comprises about 8%, by weight of the photoactivator, of photoactive moiety.

Naphthalene-mPEG(500) Carbamate Conjugate

1-Naphthyl isocyanate (0.338 g) and poly(ethylene glycol) methyl ether (mPEG-550, 1.30 g; $M_n$ ca 550, $T_m$=20° C.) were combined in 10 mL flask with a magnetic stir bar under an argon atmosphere, covered with foil to shield from light, and stirred at room temperature for 4 days. The mixture is diluted into 80 mL of water and stirred for 15 minutes. The cloudy solution is suction filtered through #3 filter paper to give a clear aqueous solution. This solution is freeze-dried to yield 1.65 g of a colorless oil which is diluted with water to provide a 0.0412 g/mL solution. The resulting photoactivator exhibits a suitable excitation wavelength of about 337 nm and comprises about 23%, by weight of the photoactivator, of photoactive moiety.

Poly(Acrylic Acid) Functionalized with Acridine Amide

Weighed out 0.427 g of 9-aminoacridine into a 25 mL 2-neck round-bottom flask with a magnetic stir bar and placed under an argon atmosphere. Added 10 mL of dioxane and stirred the resulting suspension overnight at room temperature under argon. Triethylamine (0.50 mL) is added to the 9-aminoacridine/dioxane suspension. A 25 mL 2-neck round-bottom flask with a thermocouple probe and a magnetic stir bar is charged with 4.00 g of poly(acryloyl chloride) solution (25% in dioxane, thus 1.00 g of polymer; polymer MW ~10,000) and placed under an argon atmosphere and cooled to 8° C. (thickened). The cold bath is removed and then 9-aminoacridine/dioxane slurry is added in one portion through a funnel and the mixture is left under an argon atmosphere. The mixture became thick with solids immediately; the temperature rose to 25° C. and subsided over 5 minutes. To aid stirring 5 mL more dioxane is added. The mixture is heated to 80° C. and stirring is continued under argon for 23 hours. The solids that were adhering to the sides of the flask were scraped and the entire contents were transferred to a 500 mL with the aid of 12.8 mL of 1.0 N sodium hydroxide solution and the mixture is magnetically stirred overnight. An additional 2.0 mL of 1.0 N sodium hydroxide is added to the pH 7-8 suspension of fine solids. An hour later an additional 2.0 mL of 1.0 N sodium hydroxide is added to the pH 9 suspension (less suspended solids now). After the resulting pH 11 mixture is stirred at room temperature for 3 days the pH dropped to 9-10. The sample is concentrated under reduced vacuum (rotary evaporator, 40° C.). After 50 mL of water is added to the residue it is concentrated again, and this step is repeated. The residue is suspended in 100 mL of water and suction filtered through #4 paper. The cloudy filtrate is diluted with water to 300 mL and filtered through #4 paper topped with a glass fiber pad to provide a clearer solution which is freeze-dried. The resulting 1.15 g of yellow, sticky, fibrous solid is diluted with water to provide a 0.0144 g/mL solution. The resulting photoactivator exhibits a suitable excitation wavelength of about 395 nm and comprises about 31%, by weight of the photoactivator, of photoactive moiety.

Poly(Acrylic Acid) Functionalized with Naphthalenemethyl Amide

A 25 mL 2-neck round-bottom flask with a magnetic stir bar is charged with 4.00 g of poly(acryloyl chloride) solution (25% in dioxane, thus 1.00 g of polymer; polymer MW ~10,000) and placed under an argon atmosphere. A solution of 0.346 g of 1-naphthylenemethylamine and 0.32 mL of triethylamine in 2 mL of tetrahydrofuran is added to the polymer/dioxane mixture over 5 minutes with stirring. The solution quickly forms a suspension of solids. After stirring for 24 hours at room temperature the reaction is transferred to a 100 mL flask and 19.8 mL of 1.0 M aqueous sodium hydroxide is added, the flask is capped (not under argon), and the cream-colored slurry is stirred for 16.5 hours at room temperature. After adding 2 mL of 1.0 N hydrochloric acid the mixture is concentrated under reduced pressure (rotary evaporator) at 40° C., suspended again in 50 mL of water and concentrated down to about 30 mL to give a suspension having a pH of 7-8. Subsequent addition of 1.0 mL of 1.0 N NaOH is followed by the drop wise addition of 1.0 N hydrochloric acid (approximately 1 mL) until the pH is between 9 and 10. An additional 30 mL of water is added and the mixture is concentrated under reduced pressure (rotary evaporator) at 50° C. to give 2.14 g of residue. This residue is partially dissolved/suspended in 100 mL of water and insolubles were removed by suction filtration. The resulting pH 7-8 solution is freeze-dried to give 1.78 g of an off-white, sticky, fibrous solid which is diluted with water to provide a 0.022 g/mL solution. The resulting photoactivator exhibits a suitable excitation wavelength of about 320 nm and comprises about 1%, by weight of the photoactivator, of photoactive moiety.

Fluorescein-mPEG(550) Conjugate

Fluorescein 5-isothiocyanate (0.226 g) and poly(ethylene glycol) methyl ether (mPEG-550, 1.20 g; $M_n$ ca 550, $T_m$=20° C.) were combined in 10 mL flask with a magnetic stir bar under an argon atmosphere. The mixture is placed in a 120° C. oil bath and stirred to provide an orange suspension. After 6 days at this temperature the mixture is nearly homogenous and is allowed to cool to room temperature. The residue is taken up in 100 mL of water, and after 18 hours the solution is centrifuged to remove undissolved materials. The supernatant is separated and the water is removed by freeze-drying to give 1.051 g of yellow oil which is taken up in water to provide a 0.0104 g/mL solution of the conjugate. The resulting photoactivator exhibits a suitable excitation wavelength of about 490 nm and comprises about 41%, by weight of the photoactivator, of photoactive moiety.

Fluorescein-mPEG(2000) Conjugate

Fluorescein 5-isothiocyanate (0.226 g) and poly(ethylene glycol) methyl ether (mPEG-2000, 1.500 g; $M_n$ ca 2000, $T_m$=52° C.) were combined in 10 mL flask with a magnetic stir bar under an argon atmosphere. The mixture is placed in a 100° C. oil bath and stirred as the mPEG-2000 melted to provide an orange suspension. After 3 days at this temperature the mixture is nearly homogenous and is allowed to cool to room temperature. The residue is taken up in 200 mL of water, and after 18 hours undissolved solids were removed by vacuum filtration. The water is removed by freeze-drying to give 1.514 g of yellow-orange solid which is taken up in water to provide a 0.014 g/mL solution of the conjugate. The resulting photoactivator exhibits a suitable excitation wavelength of about 460 nm and comprises about 12%, by weight of the photoactivator, of photoactive moiety.

Gantrez-Aminoacridine Amide Conjugate

A 250 mL round-bottom flask is charged with 0.972 g of 9-aminoacridine and 23 ml THF. Stir under nitrogen while cooling in an ice water bath. Via a dry syringe transfer 1.5 ml of 2.5M butyllithium solution in hexanes to the flask. Remove the ice bath and continue to stir for 20 min at RT. Weigh out 2.925 g of Gantrez (anhydride form; $M_w$ 216,000; $M_n$ 80,000), and add 140 ml THF. Some material remained undissolved. Pour the mixture into the into the reaction flask at RT. Add 1 ml triethylamine. Heat to reflux. Continue to reflux for 35 days then cool to RT. An aqueous solution of 1.0 N sodium hydroxide (35 mL) is slowly added to reaction flask and the mixture is stirred another 16 hours at room temperature. The two-phase mixture is transferred to a 1 L flask with 100 mL of water and concentrated at 50° C. in vacuo using a rotary evaporator. Three additional cycles were performed adding 50 mL of water and concentrating to give 6.7 g of a tan/beige solid. This residue is taken up in 200 mL of water, suction filtered, and the filtrate is freeze-dried to provide 6.55 g of a light solid. An aliquot 1.0139 g of this sample is diluted with 20 ml of $H_2O$ to give a 5 wt % aqueous solution.

Phenothiazine-mPEG(2000) Carbamate Conjugate

To a 250 mL round-bottom flask containing a magnetic stir bar and fitted with a condenser connected to a Firestone valve (for vacuum and nitrogen introduction) is charged with 7.58 g of poly(ethylene glycol) methyl ether (mPEG-2000, $M_n$ ca 2000, $T_m$=52° C.) and 90 mL of methylene chloride at RT. While stirring under nitrogen 1.0009 g Phenothiazine-10-carbonyl chloride is added at room temperature. The colorless solution changed to a pink color with some precipitation. To the mixture is added 0.0471 g of 4-(dimethylamino)pyridine and 0.58 mL of triethylamine. The mixture is heated to reflux for 96 hours. The mixture became darker and a slurry observed at the bottom of the flask. After cooling and adding an additional 50 mL of methylene chloride the mixture is extracted with 20 mL of 1M HCl and twice with 50 mL of water. The organic solution is dried over magnesium sulfate. After suction filtering the solvent is removed in vacuo at 46° C. using a rotary evaporator. The solid (9.10 g) residue is taken up in 400 mL of water to provide a milky white solution which is suction filtered through a combination of glass and paper fiber filter pads. Freeze-drying led to 7.16 g of a pure white solid. An aliquot of the solid 1.0085 g is dissolved in 10 ml $H_2O$ to make a 10 wt. % aqueous solution.

Gantrez-Naphthoic Hydrazide Diacylhydrazine Conjugate

A 250 mL round-bottom flask containing 4.20 g of Gantrez (anhydride form; $M_w$ 216,000; $M_n$ 80,000), 125 mL of tetrahydrofuran, and a magnetic stir bar is fitted with a condenser connected to a Firestone valve (for vacuum and nitrogen introduction) and stirred at RT under nitrogen. The polymer dissolved. The flask is then charged with 1-Naphthoic hydrazide 1.0019 g, and triethylamine 0.60 g at RT. Initially all the reagents were in solution, but became a purple color mixture over time. The mixture is heated to reflux for 48 hours, then cool to RT. An aqueous solution of 1.0 N sodium hydroxide (48.5 mL) is slowly added to reaction and the mixture is stirred another 16 hours at room temperature. The two-phase mixture is transferred to a 1 L flask with 100 mL of water and 50 ml THF and concentrated at 50° C. in vacuo using a rotary evaporator. Three additional cycles were performed adding 75 mL of water and concentrating to give 7.72 g of a tan/beige solid. This residue is taken up in 200 mL of water, suction filtered, and the filtrate is freeze-dried to provide 6.63 g of a light solid. An aliquot 1.07 g of this sample is diluted to a 10 wt % aqueous solution.

Each of the photoactivators exemplified above are found to be suitable photoactivators according to both the CHLORITE QUENCHING TEST METHOD and the INDIGO CARMINE BLEACHING TEST METHOD, as described hereinbefore.

It should be understood that every maximum numerical limitation given throughout this specification would include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A photoactivator comprising:
  a) a photoactive moiety selected from the group consisting of 1,1'-biphenyl-4,4'-diamine, 1,1'-biphenyl-4-amine, benzophenone, 1,1'-biphenyl-4,4'-diol, 1,1'-biphenyl-4-amine, 1,1'-biphenyl-4-ol, 1,1':2',1"-terphenyl, 1,1':3',1"-terphenyl, 1,1':4'1":4",1'''-quaterphenyl, 1,1':4',1"-terphenyl, 1,10-phenanthroline, 1,1'-biphenyl, 1,2,3,4-dibenzanthracene, 1,2-benzenedicarbonitrile, 1,3-isobenzofurandione, 1,4-naphthoquinone, 1,5-naphthalenediol, 10H-phenothiazine, 10H-phenoxazine, 10-methylacridone, 1-acetonaphthone, 1-chloroanthraquinone, 1-hydroxyanthraquinone, 1-naphthalenecarbonitrile, 1-naphthalenecarboxaldehyde, 1-naphthalenesulfonic acid, 1-naphthalenol, 2(1H)-quinolinone, 2,2'-biquinoline, 2,3-naphthalenediol, 2,6-dichlorobenzaldehyde, 21H,23H-porphine, 2-aminoanthraquinone, 2-benzoylthiophene, 2-chlorobenzaldehyde, 2-chlorothioxanthone, 2-ethylanthraquinone, 2H-1-benzopyran-2-one, 2-methoxythioxanthone, 2-methyl-1,4-naphthoquinone, 2-methyl-9(10-methyl)-acridinone, 2-methylanthraquinone, 2-methylbenzophenone, 2-naphthalenamine, 2-naphthalenecarboxylic acid, 2-naphthalenol, 2-nitro-9(10-methyl)-acridinone, 9(10-ethyl)-acridinone, 3,6-qcridinediamine, 3,9-dibromoperylene, 3,9-dicyanophenanthrene, 3-benzoylcoumarin, 3-methoxy-9-cyanophenanthrene, 3-methoxythioxanthone, 3'-methylacetophenone, 4,4'-dichlorobenzophenone, 4,4'-dimethoxybenzophenone, 4-bromobenzophenone, 4-chlorobenzophenone, 4'-fluoroacetophenone, 4-methoxybenzophenone, 4'-methylacetophenone, 4-methylbenzaldehyde, 4-methylbenzophenone, 4-phenylbenzophenone, 6-methylchromanone, 7-(diethylamino)coumarin, 7H-benz[de]anthracen-7-one, 7H-benzo[c]xanthen-7-one, 7H-furo[3,2-g][1]benzopyran-7-one, 9(10H)-acridinone, 9(10H)-anthracenone, 9(10-methyl)-acridinone, 9(10-phenyl)-acridinon, 9,10-anthracenedione, 9-acridinamine, 9-cyanophenanthrene, 9-fluorenone, 9H-carbazole, 9H-fluoren-2-amine, 9H-fluorene, 9H-thioxanthen-9-ol, 9H-thioxanthen-9-one, 9H-thioxanthene-2,9-diol, 9H-xanthen-9-one, acetophenone, acridene, acridine, acridone, anthracene, anthraquinone, anthrone, α-tetralone, benz[a]anthracene, benzaldehyde, benzamide, benzo[a]coronene, benzo[a]pyrene, benzo[f]quinoline, benzo[ghi]perylene, benzo[rst]pentaphene, benzophenone, benzoquinone, 2,3,5,6-tetramethyl, chrysene, coronene, dibenz[a,h]anthracene, dibenzo[b,def]chrysene, dibenzo[c,g]phenanthrene, dibenzo[def,mno]chrysene, dibenzo[def,p]chrysene, DL-tryptophan, fluoranthene, fluoren-9-one, fluorenone, isoquinoline, methoxycoumarin, methylacridone, michler's ketone, naphthacene, naphtho[1,2-g]chrysene, N-methylacridone, p-benzoquinone, p-benzoquinone, 2,3,5,6-tetrachloro, pentacene, phenanthrene, phenanthrenequinone, phenanthridine, phenanthro[3,4-c]phenanthrene, phenazine, phenothiazine, p-methoxyacetophenone, pyranthrene, pyrene, quinoline, quinoxaline, riboflavin 5'-(dihydrogen phosphate), thioxanthone, thymidine, xanthen-9-one, xanthone, and mixtures thereof; and b) a hydrophilic moiety selected from the group consisting of alkylene oxide oligimers, alkylene oxide polymers, alkylene oxide copolymers, ethylene glycol, vinyl alcohol, vinyl pyrrolidone, acrylic acid, methacrylic acid, cellulose, carboxymethyl cellulose, chitosan, dextran, polysaccharides, 2-ethyl-2-oxazoline, hydroxyethyl methacrylate, vinyl pyridine-N-oxide, diallyl dimethyl ammonium chloride, maleic acid, lysine, styrene sulfonic acid, vinyl methyl ether, vinyl phosphoinic acid, ethylene imine, and mixtures thereof, wherein the photoactivator comprises less than 10%, by weight, of the photoactive moiety; and wherein the photoactivator is activated to a photo-excited state by excitation with exposure to incident radiation of a wavelength between about 350 nm and 750 nm.

2. The photoactivator of claim 1, wherein the photoactivator comprises less than about 5%, by weight, of the photoactive moiety.

3. The photoactivator of claim 1, wherein the photoactivator comprises less than about 2%, by weight, of the photoactive moiety.

4. The photoactivator of claim 1, wherein the photoactivator is activated to a photo-excited state by excitation with exposure to incident radiation of a wavelength between about 350 nm and about 420 nm.

5. The photoactivator of claim 1, wherein the photo-excited state of the photoactivator has an energy greater than about 100 kJ/mol more than a ground state of the photoactivator.

6. The photoactivator of claim 1, wherein the photoactive moiety is selected from the group consisting of xanthone, xanthene, thioxanthone, thioxanthene, phenothiazine, fluorescein, benzophenone, alloxazine, isoalloxazine, flavin, and mixtures thereof.

7. The photoactivator of claim 1, wherein the photoactive moiety is thioxanthone.

8. The photoactivator of claim 1, wherein the hydrophilic moiety is selected from the group consisting of alkylene oxide oligimers, alkylene oxide polymers, alkylene oxide copolymers, ethylene glycol, vinyl alcohol, vinyl pyrrolidone, acrylic acid, methacrylic acid, ethylene imine, and mixtures thereof.

* * * * *